United States Patent [19]

Kim

[11] Patent Number: 4,721,579

[45] Date of Patent: Jan. 26, 1988

[54] SODIUM CARBOXYMETHYL DERIVATIVES OF POLYOXYALKYLENE GLYCOLS, THEIR PRODUCTION, AND USE IN FUNCTIONAL FLUIDS

[75] Inventor: Bongsub Kim, Grosse Ile, Mich.

[73] Assignee: BASF Corporation, Parsippany, N.J.

[21] Appl. No.: 178,267

[22] Filed: Aug. 15, 1980

[51] Int. Cl.$^4$ .................. B01J 13/00; C07C 59/245; C09K 5/00
[52] U.S. Cl. ........................... 252/79; 252/73; 252/75; 252/315.4; 514/941; 562/587; 568/618; 568/625
[58] Field of Search ............. 252/316, 79, 315.4; 562/587; 568/618, 625

[56] References Cited

U.S. PATENT DOCUMENTS

| | | | |
|---|---|---|---|
| 2,745,857 | 5/1956 | Britton et al. | 562/587 X |
| 3,240,819 | 3/1966 | Gaertner et al. | 252/108 X |
| 3,278,585 | 10/1966 | Baker et al. | 252/79 X |
| 3,748,276 | 7/1973 | Schmolka | 252/316 |
| 3,992,443 | 11/1976 | Springmann | 562/587 |
| 4,098,818 | 7/1978 | Krummel et al. | 260/501.17 X |
| 4,288,639 | 9/1981 | Camp | 568/625 |
| 4,312,768 | 1/1982 | Nassry et al. | 568/624 X |

FOREIGN PATENT DOCUMENTS 793113  4/1958  United Kingdom ............ 562/587

Primary Examiner—Richard D. Lovering
Attorney, Agent, or Firm—Joseph D. Michaels; Bernhard R. Swick

[57] ABSTRACT

A new type of ionic thickener for water-based products including functional fluids such as hydraulic fluids, cosmetic emulsions, etc. These new thickeners are prepared from polyoxyalklylene glycols, higher alkyl monoepoxides, lower alkyl monohalo lower alkyl carboxylates, and alkali metal hydroxide. These novel thickeners are generally characterized by the following formula:

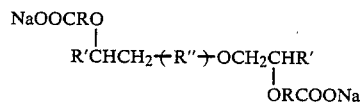

wherein R is a methylene or lower polymethylene group, R' is a higher alkyl group and R" is selected from the group consisting of oxyethylene groups and heteric or block copolymer mixtures of oxyethylene and other lower oxyalkylene groups, said copolymer containing at least 75 percent oxyethylene groups.

9 Claims, No Drawings

SODIUM CARBOXYMETHYL DERIVATIVES OF POLYOXYALKYLENE GLYCOLS, THEIR PRODUCTION, AND USE IN FUNCTIONAL FLUIDS

BACKGROUND OF THE INVENTION

1. Field of the Invention

This invention relates to new polyoxyalkylene derivatives which possess an excellent thickening property and to the preparation of such polyoxyalkylene derivatives. These products are useful as stable thickening agents for use in hydraulic fluids, textile printing emulsions, cosmetic emulsions, aqueous pigment suspensions and other emulsified or dispersed systems.

2. Description of the Prior Art

Polymeric water-soluble thickening agents are widely used for many purposes. Commercially-available polymeric thickeners differ widely in chemical composition. The diversity of available thickening agents is an indication that not all are equally useful. It is not unusual to find some thickening agents which perform well in a certain environment and not at all in another. In fact, in some uses no one thickening agent is completely satisfactory and there is a continual need and a continuing search for new thickening agents to satisfy many unmet needs. For instance, various cellulose derivatives or other water-soluble polymers such as sodium polyacrylates, polyacrylamides and polyethylene glycol fatty acid diesters are representative thickening agents. The polyethylene glycol fatty acid diesters are widely used for textile printing emulsions, cosmetic emulsions and aqueous pigment suspension. These esters suffer from the defect that they are not resistant to hydrolysis in an acid or alkaline medium so that under such conditons, the thickening effect initially obtained is gradually reduced.

Polyoxyalkylene compounds, including high molecular weight materials, are well known for use as surface-active agents as disclosed in U.S. Pat. No. 2,674,619. These compositions can be prepared at high molecular weights, for instance, up to 25,000 for use as aqueous thickeners. It is known that liquid polyoxyalkylene can be obtained by utilizing a mixture of ethylene oxide and another lower alkylene oxide in an oxide ratio of 75 to 90 percent ethylene oxide and 10 to 25 percent other lower alkylene oxides such as propylene oxide as taught in U.S. Pat. No. 2,425,755.

RELEVANT PATENTS AND APPLICATIONS

U.S. Pat. Nos. 3,538,033; 2,990,396; 4,098,818; 3,992,443; 3,983,171; 3,959,460; 2,791,551; and 2,183,853; and U.S. Ser. No. 86,837 now U.S. Pat. No. 4,288,639.

SUMMARY OF THE INVENTION

It is the purpose of the instant invention to provide a new type of ionic thickener for water-based products including functional fluids such as hydraulic fluids, cosmetic emulsions, etc. These new thickeners are prepared from polyoxyalkylene glycols, higher alkyl monoepoxides, lower alkyl monohalo lower alkyl carboxylates, and alkali metal hydroxide.. The polyoxyalkylene glycols are either polyoxyethylene glycol or polyoxyethylene copolymers with lower alkylene oxides having 3 to 4 carbon atoms containing at least 75 percent oxyethylene groups. These novel thickeners are generally characterized by the following formula:

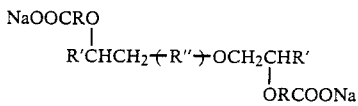

wherein R is a methylene or lower polymethylene group, R' is a higher alkyl group and R" is selected from the group consisting of straight-chain oxyethylene groups and heteric or block copolymer mixtures of oxyethylene and other lower oxyalkylene groups, said copolymer containing at least 75 percent oxyethylene groups.

The above composition has a molecular weight of about 4000 to 25,000.

The new thickeners exhibit an unexpected increased thickening efficiency in aqueous systems as compared with some prior art polyether thickeners of the same molecular weight.

DETAILED DESCRIPTION OF THE INVENTION

Polyether thickening agents having greatly improved thickening ability can be obtained by modifying conventional polyether thickening agents, particularly polyethylene glycol thickening agents, and copolymer thickening agents of ethylene oxide and lower alkylene oxides; with higher alkyl monoepoxide and alkali metal carboxy lower alkyl groups. The polyether thickening agent of this invention is a 4000-25,000 molecular weight compound generally having the formula:

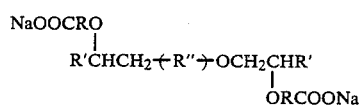

wherein R is a methylene or lower polymethylene group; R' is a higher alkyl group; and R" is selected from the group consisting of straight-chain oxyethylene groups and heteric or block copolymer mixtures of oxyethylene and other lower oxyalkylene groups, at least about 75 percent of said copolymer groups being oxyethylene groups. In this type of compound, the viscosity can be controlled by the length of the polyoxyalkylene chain, i.e., the group R", and the length of the higher alkyl group R'.

It is preferred that the R groups contain 1 to about 4 carbon atoms, and that the R' groups contain about 8 to 28 aliphatic carbon atoms and that R" contain about 90 to 450 oxyalkylene groups.

The above thickeners were prepared from polyoxyalkylene glycols, by adding higher alkyl monoepoxide to each end of said glycol and adding alkali metal carboxy lower alkyl groups to each end of the resulting polymer. It has been discovered in accordance with this invention that alkali metal alcoholates of the polyoxyalkylene glycol reactant made using metallic sodium or potassium generally in stoichiometric amounts promote the reaction of the higher alkyl monoepoxide and the polyoxyalkylene glycol. Also, it has been found that the compound is best prepared by reacting the reaction product of the polyoxyalkylene glycol and higher alkyl epoxide with a lower alkyl monohalo lower alkyl carboxylate and then saponifying the product with an alcoholic alkali metal hydroxide. A lower alcohol such as methyl alcohol is preferred. Accordingly, in accordance with the instant invention, a process is provided for producing a high molecular weight polymeric product which comprises reacting a high molecular weight polyoxyalkylene glycol of the type described above with an alkali metal such as metallic sodium or potassium, reacting the product of this reaction with a higher alkyl monoepoxide, and reacting the product thereof with a lower alkyl monohalo lower alkyl carboxylate and an alcoholic alkali metal hydroxide.

The preparation of polyethers such as the polyoxyalkylene glycols employed in this invention is well known in the art. Generally, they are prepared utilizing the lower alkylene oxide which is ethylene oxide or mixtures of ethylene oxide with other lower alkylene oxides having 3 or 4 carbon atoms and an active hydrogen-containing compound which, in the instant case, would preferably be ethylene glycol, in the presence of an acidic or basic oxyalkylation catalyst at elevated temperatures in the range of about 50° C. to 150° C. under an inert gas pressure generally from about 20 to 100 pounds per square inch gauge.

Alkaline catalysts such as potassium hydroxide or acid catalysts such as boron trifluoride are useful for catalyzing the above reactions as is well established in the art of preparing polyethers.

The higher alkyl monoepoxides utilized to modify the polyoxyalkylene glycols specified above generally contain about 10 to 30, and preferably about 12 to 20, aliphatic carbon atoms and commercially-available mixtures thereof. Examples of useful epoxide compounds are the following: 1,2-epoxydecane, 1,2-epoxydodecane, 1,2-epoxytetradecane, 1,2-epoxyhexadecane, 1,2-epoxyoctadecane, 1,2-epoxyeicosane, a blend of 1,2-epoxyalkanes ($C_{11}$, $C_{12}$, $C_{13}$, $C_{14}$), a blend of 1,2-epoxyalkanes ($C_{15}$, $C_{16}$, $C_{17}$, $C_{18}$), and a blend of 1,2-epoxyalkanes ($C_{20}$, $C_{22}$, $C_{24}$) and a blend of 1,2-epoxyalkanes ($C_{24}$, $C_{26}$, $C_{28}$, $C_{30}$).

The amount of the epoxide compound required to obtain the more efficient thickening agents of the invention is about 2 to about 15 percent, preferably about 5 to 10 percent, by weight of the polyoxyalkylene glycol.

The lower alkyl monohalo lower alkyl carboxylates employed in the instant invention are generally those wherein both lower alkyl groups have from 1 to 4 carbon atoms. Particularly preferred are methylmonochloroacetate and ethylmonochloroacetate. The amount of lower alkyl monohalo lower alkyl carboxylate required to obtain the more efficient thickening agents of the invention is about 2 to about 10 percent, preferably about 3 to 6 percent, by weight of the polyoxyalkylene glycol.

Suitable alkali hydroxides are lithium, sodium and potassium hydroxides. In general, however, sodium hydroxide is used for economic reasons.

In the preferred method of preparing the thickeners of this invention, the polyoxyalkylene glycol is reacted with sodium at a temperature ranging from 20° C. to 200° C. for 0.5 to 10 hours in an amount of about 0.1 to 2 percent by weight of the polyoxyalkylene glycol. The epoxide is then added and reacted at a temperature from 50° C. to 200° C. for about 0.5 to 10 hours. The lower alkyl monohalo lower alkyl carboxylate is then added and reacted at a temperature of 20° C. to 150° C. for a period ranging from 10 minutes to 5 hours. The product is then saponified by refluxing with a mixture of about 0.5 to 5 percent sodium hydroxide based on the weight of the polyoxyalkylene glycol in alcohol for 0.5 to 10 hours.

In general, aqueous systems employing the thickeners of the instant invention, particularly functional fluids such as hydraulic fluids, are prepared by adding from about 2 to 10 percent by weight of the thickener of the instant invention to the aqueous fluid. Generally a conventional water-glycol hydraulic fluid contains about 30 to 50 percent by weight water, balance normal ingredients of a hydraulic fluid.

The following examples illustrate the preparation of the thickener of the instant invention.

EXAMPLE I

Four hundred and ninety grams (0.12 mole) of a 4000 molecular weight polyoxyethylene glycol was freed from moisture under oil pump vacuum, in a molten state, with the bath maintained at 110° C. Sodium was added under vigorous stirring at 100° C. in an amount of 5.6 grams (0.24 mole) to produce the sodium polyoxyethylene glycolate. After complete reaction of the sodium requiring approximately 8 hours, 57.6 grams (0.24 mole) of 1,2-epoxyhexadecane was added and reacted at 100° C. for 8.5 hours. Ethylmonochloroacetate was then added in amount of 29.3 grams (0.24 mole) and reacted at 90° C. to produce the ester which was then saponified by the addition of 9.7 grams (0.24 mole) of sodium hydroxide. A 10 percent aqueous solution of the product was made up and the viscosity tested at 100° F. and a pH of 9.5 and was found to be 20.4 centipoises. The cloud point was determined for the 10 percent aqueous solution and found to be greater than 100° C.

EXAMPLE II

A thickener was prepared employing the same procedure as Example I with the exception that the polyoxyethylene glycol is employed in amount of 250 grams (0.06 mole). Also, 33.1 grams (0.12 mole) of 1,2-epoxyoctadecane was employed in lieu of the 1,2-epoxyhexadecane and 2.8 grams (0.12 mole) of sodium, 15.1 grams (0.12 mole) of ethylmonochloroacetate, and 4.9 grams (0.12 mole) of sodium hydroxide were employed in lieu of the amounts stated in Example I. A 10 percent aqueous solution of the product was tested for viscosity at 100° F. and a pH of 10 and found to have a viscosity of 51.3 centipoises. The cloud point of the product was tested and found to be greater than 100° C.

EXAMPLE III

A thickener was prepared employing the same procedure as Example II with the exception that 500 grams (0.066 mole) of a 7600 molecular weight polyoxyethylene glycol was employed in lieu of the 4000 molecular weight polyoxyethylene glycol. Also, 3.0 grams (0.13 mole) of sodium, 35.5 grams (0.13 mole) of 1,2-epoxyoctadecane, 16.2 grams (0.13 mole) of ethylmonochloro acetate, and 5.3 grams (0.13 mole) of sodium hydroxide were employed in lieu of the amounts stated in Example II. The viscosity of the product was determined on a 10 percent aqueous solution at 100° F. and a pH of 10 and found to be 2300 centipoises. The cloud point was determined and found to be greater than 100° C.

EXAMPLE IV

A thickener was prepared in accordance with the procedure set forth above in Example III with the exception that after the complete reaction of the sodium to produce the sodium polyoxyethylene glycolate, 3.8 grams (0.019 mole) of 1,4-butanediol diglycidyl ether was added to the sodium polyoxyethylene glycolate to extend the chain, the reaction temperature being maintained at 95° C. and requiring 8.5 hours. In addition, 282 grams (0.037 mole) of the polyoxyethylene glycol, 1.7 grams (0.074 mole) of sodium, 20.1 grams (0.075 mole) of the 1,2-epoxyoctadecane, 9.2 grams (0.075 mole) of the monochloroacetate and 3.0 grams (0.075 mole) of sodium hydroxide were employed in lieu of the amounts set forth in Example III. The viscosity of a 6 percent aqueous solution of the product was determined at 100° F. and a pH of 9 and found to have a viscosity of 2056 centipoises. The cloud point was also determined on this solution and found to be greater than 100° C.

Where not otherwise specified throughout this specification and claims, temperatures are given in degrees Centigrade and parts, percentages and proportions are by weight.

While this invention has been described with reference to certain specific embodiments, it will be recognized by those skilled in the art that many variations are possible without departing from the spirit and scope of the invention and it will be understood that it is intended to cover all changes and modifications of the invention disclosed herein for purpose of illustration which do not constitute departures from the spirit and scope of the invention.

The embodiments of the invention in which an exclusive privilege or property is claimed are defined as follows:

1. A 4000 to, 20,000 molecular weight polyoxyalkylene polymer thickener characterized by the following formula:

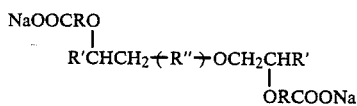

wherein R is a methylene or lower polymethylene group, R' is a higher alkyl group, and R" is a chain of lower oxyalkylene groups.

2. The polymer of claim 1 wherein the R groups contain about 1 to 4 carbon atoms, the R' groups contain about 8 to 28 aliphatic carbon atoms, and R" contains about 90 to 450 oxyalkylene groups which are oxyethylene groups or heteric or block copolymers of oxyethylene and lower oxyalkylene groups having about 3 to 4 carbon atoms, said copolymers containing at least about 75 percent oxyethylene groups.

3. The polymer of claim 1 wherein R is a methylene group, and R" is all oxyethylene groups.

4. In an aqueous functional fluid the improvement wherein said functional fluid includes an effective thickening amount of the polymeric product of claim 1.

5. The improved functional fluid of claim 4 wherein the R groups of said polymeric product contain about 1 to 4 carbon atoms, the R' groups contain about 8 to 28 aliphatic carbon atoms, and R" contains about 90 to 450 oxyalkylene groups which are straight chain oxyethylene groups or heteric or block copolymers of oxyethylene and lower oxyalkylene groups having about 3 to 4 carbon atoms, said copolymers containing at least about 75 percent oxyethylene groups.

6. The improved functional fluid of claim 5 wherein R is a methylene group, and R" is all oxyethylene groups.

7. A process for producing a polymeric thickener product having a molecular weight of about 4,000 to 25,000 which comprises reacting a high molecular weight polyoxyethylene glycol containing about 90 to 450 oxyethylene groups or a heteric or block polyoxyethylene copolymer with lower alkylene oxides having about 3 to 4 carbon atoms and containing at least about 75 percent oxyethylene groups with an alkali metal, reacting the product thereof with a higher alkyl monoepoxide containing about 10 to 30 aliphatic carbon atoms, reacting the latter product with a lower alkyl monohalo lower alkyl carboxylate containing about 1 to 4 carbon atoms, and an alkali metal hydroxide.

8. The process of claim 7 wherein the polyoxyalkylene glycol is reacted with the alkali metal at a temperature of about 20° to 200° C. for about 0.5 to 10 hours, the epoxide is reacted at a temperature from about 50° to 200° C. for about 0.5 to 10 hours, the lower alkyl monohalo lower alkyl carboxylate is reacted at a temperature of about 20° C. to 150° C. for a period of about 10 minutes to 5 hours, and the product is saponified with the alkali metal hydroxide for about 0.5 to 10 hours.

9. The process of claim 8 wherein said polyoxyalkylene glycol is polyoxyethylene glycol, said lower alkyl monohalo lower alkyl carboxylate is ethylmonochloroacetate, and said alkali metal in both the first and last steps is sodium.

* * * * *